United States Patent
Baba et al.

(10) Patent No.: US 6,595,685 B2
(45) Date of Patent: Jul. 22, 2003

(54) METHOD AND APPARATUS FOR MEASURING THERMOPHYSICAL PROPERTIES

(75) Inventors: Tetsuya Baba, Ibaraki (JP); Naoyuki Taketoshi, Ibaraki (JP); Kimihito Hatori, Ibaraki (JP); Tetsuya Otsuki, Ibaraki (JP)

(73) Assignees: National Research Laboratory of Metrology, Tsukuba (JP); Kabushiki Kaisha Bethel, Ishioka (JP)

( * ) Notice: Subject to any disclaimer, the term of this patent is extended or adjusted under 35 U.S.C. 154(b) by 0 days.

(21) Appl. No.: 09/416,993

(22) Filed: Oct. 13, 1999

(65) Prior Publication Data

US 2002/0131476 A1 Sep. 19, 2002

(30) Foreign Application Priority Data

Oct. 13, 1998 (JP) ............................................. 10-290555

(51) Int. Cl.[7] .............................................. G01K 11/00
(52) U.S. Cl. .......................... 374/161; 374/43; 374/120
(58) Field of Search .......................... 374/43, 120, 161, 374/17, 18, 19, 20

(56) References Cited

U.S. PATENT DOCUMENTS

| | | | | |
|---|---|---|---|---|
| 4,513,384 A | * | 4/1985 | Rosencwaig | 364/563 |
| 4,579,463 A | * | 4/1986 | Rosencwaig et al. | 374/57 |
| 4,671,651 A | * | 6/1987 | Toyoda et al. | 374/161 |
| 4,679,946 A | * | 7/1987 | Rosencwaig et al. | 374/5 |
| 4,928,254 A | * | 5/1990 | Knudsen et al. | 364/556 |
| 5,042,952 A | * | 8/1991 | Opsal et al. | 356/432 |
| 5,074,669 A | * | 12/1991 | Opsal | 356/445 |
| 5,228,776 A | * | 7/1993 | Smith et al. | 374/5 |
| 5,844,684 A | * | 12/1998 | Maris et al. | 356/432 |

FOREIGN PATENT DOCUMENTS

| WO | WO 9924841 A | * | 5/1999 | G01M/11/00 |
|---|---|---|---|---|

OTHER PUBLICATIONS

Naoyuki Taketoshi, Tetsuya Baba, and Akira Ono, "Development Of A Thermal Diffusivity Measurement System With A Picosecond Thermoreflectance Technique", 29 High Temperatures—High Pressures, 59–66 (1997).

N. Taketoshi, T. Baba, and A. Ono, "Picosecond Thermoreflectance Measurements of Thermal Diffusion in Film/Substrate Two–Layer Systems", Thermo Conductivity 24, 289–302 (Oct. 26–29, 1997).

N. Taketoshi, M. Ozawa, H. Ohta, and T. Baba, "Thermal Effusivity Distribution Measurements Using A Thermoreflectance Technique", Photoacoustic and Photothermal Phenomena Tenth International Conference, 315–17 (Aug., 1998).

Tetsuya Baba, Naoyuki Taketoshi, and Akira Ono, "Analysis of Thermal Diffusion In Multi–Layer Thin Films By A Response Function Method", The Nineteenth Japan Symposium on Thermophysical Properties, 231–34 (1998).

Naoyuki Taketoshi, Tetsuya Baba, and Akira Ono, "Observation of Heat Diffusion Across Submicrometer Metal Thin Films Using A Picosecond Thermoreflectance Technique", 38 Japanese Journal of Applied Physics, No. 11A, L1268–71 (Nov., 1999).

* cited by examiner

*Primary Examiner*—Diego Gutierrez
*Assistant Examiner*—Lydia M. De Jesús
(74) *Attorney, Agent, or Firm*—Morgan & Finnegan, LLP

(57) ABSTRACT

An apparatus and method for measuring thermophysical property value of a specimen. The apparatus includes a heating laser and probe laser for measuring at least one characteristic on the surface of the specimen. A detector detects the reflected probe laser beam, and a computer calculates the thermophysical property value of the specimen based on the reflected probe laser beam.

2 Claims, 2 Drawing Sheets

METHOD AND APPARATUS FOR MEASURING THERMOPHYSICAL PROPERTIES

BACKGROUND OF THE INVENTION

1. Field of the Invention

The invention relates generally to apparata and methods for measuring thermal effusivity distribution of micro-scale region by the thermoreflectance technique, and more particularly, for calculating the thermophysical property of specimen in micro-scale by focusing a heating laser beam and a probe laser beam at the same point on the specimen and detecting the reflection of the probe laser beam.

2. Description of the Related Art

Although the laser flash method is well established for thermal diffusivity measurements, the method requires the disk-shaped specimen have a thickness of more than 1 mm and typically 10 mm in diameter. The thermal diffusivity value measured with this method is the averaged value over the entire specimen.

However, the laser flash method is unsuitable to measure thermophysical property distribution of a smaller region, namely micro-scale (e.g., specimens having dimensions on the order of micrometers or smaller), which is especially important in modern microelectronics industries, especially in microelectronic devices, and large storage media that are increasingly complex and miniaturized for higher integration and quality.

Although thermophysical property values of small areas are needed for heat transport simulation of micro devices, in general, measurement of such values is difficult compared to measurement for bulk materials.

In the related field, thermal diffusivity measurement systems with a picosecond thermoreflectance technique have been developed to measure thermal diffusivity of submicrometer thin films. However, these systems are not suitable for thermal property distribution measurements, since the diameter of the measured area is larger than 50 micrometers and the technique takes 30 minutes to measure the value at one point.

Primary objectives of this invention are to solve the problems of these conventional techniques and to provide methods and apparata for thermal diffusivity measurement, which are capable of measuring the thermophysical property distribution of a specimen's micro-scale surface with high spatial resolution.

SUMMARY OF THE INVENTION

For achieving these objectives, one embodiment of the invention provides an apparatus for micro-scale thermophysical property measurements including a heating laser system which produces a heating laser beam that heats the surface of the specimen, a modulator which sinusoidally modulates the intensity of the heating laser beam, a probe laser system, which produces a probe laser beam that is impinged on the heated surface of the specimen, a microscopic optics that focuses both beams at the same point on the surface, a photo detector for detecting the reflection of the probe laser beam and determining the temperature change of the surface based on the temperature dependence of reflectivity at the surface, and a computer which calculates the local thermophysical property of the specimen based on the reflection detected above.

In an alternate embodiment of the invention, the apparatus calculates the thermophysical property value from the phase lag of the reflected probe beam from the heating beam.

In an alternate embodiment of the invention, the apparatus calculates the thermophysical property value from the ratio of the relative intensity difference of the reflected probe beam to that of the heating beam.

In an alternate embodiment of the invention, the apparatus coats a metallic thin film on the specimen's surface.

In yet another alternate embodiment of the present invention, the apparatus measures the two-dimensional distribution of the thermophysical property of the specimen by translating the specimen set on an X-Y stage relative to the microscopic optics.

In one embodiment of the invention, a specimen's surface is heated with a modulated heating laser beam whose spot size is only several micrometers. By focusing the heating laser beam and a probe laser beam at the same point, the phase of the surface temperature delays from the phase of the modulated heating laser beam because of the heat diffusion into the specimen. Since the reflection of the probe laser beam proportionally changes with specimen's surface temperature, the phase lag depends on the thermophysical property of the specimen. Therefore, the amplitude and the phase lag of the temperature change of the specimen's surfaced could be measured by lock-in amplifying the signal of reflection of the probe laser beam, that is detected by the photo-detector, with the reference signal. In one embodiment, the intensity of the probe laser beam proportionally changes with the surface temperature.

Since the phase lag of the surface temperature change is smaller for larger absorption coefficient, $\alpha$, and thermal diffusivity, k, $\alpha^2 k$ could be calculated from the phase lag induced by the intensity change of the reflection of probe laser beam to the heating laser beam. In one embodiment, the intensity change of the probe laser beam is proportional to the surface temperature change. Since the temperature change is larger for larger absorption coefficient, $\alpha$, and thermal diffusivity, k, $\alpha^2 k$ could be calculated from the ratio of the intensity change of probe laser beam to that of the heating laser beam. In another embodiment, even if a specimen has small absorption coefficient to the heating laser beam and small reflectivity change to the probe laser beam, the thermoreflectance technique is applicable to the specimen coating with a metal thin film of large thermoreflectance effect.

According to another embodiment of the invention, $C/b_s$ could be calculated from the phase lag of the reflected probe laser beam to the heating laser beam since the phase lag is small when the specimen has small heat capacitance, C, and large thermal effusivity, $b_s$.

According to yet another embodiment of the invention, $C/b_s$ could be calculated from the relative intensity of the probe laser beam to that of the heating laser beam.

According to still another embodiment of the invention, two-dimensional distribution of local thermophysical property could be calculated by measuring the phase lag and the relative intensity while translating the specimen set on the X-Y stage in two-dimensions.

DETAILED DESCRIPTION OF PREFERRED EMBODIMENTS

An example of the measurement system will now be explained with reference to the figures. The theory for the invention is explained first.

A film/substrate two-layer model is considered. The film and the substrate correspond to a metal thin film and specimen respectively.

Sinusoidally modulated heating laser beam with an angular frequency, $\omega$, reaches the specimen and a part of the beam's energy is absorbed on the surface which has the thickness, d, thermal diffusivity, $k_f$, and thermal effusivity, $b_f$.

The temperature response on the surface oscillates with the angular frequency, $\omega$, and a phase lag, $\delta$, to the heating laser beam.

The phase lag is smaller when the thermal effusivity of the specimen is larger or the angular frequency, $\omega$, is smaller.

Figure 1:
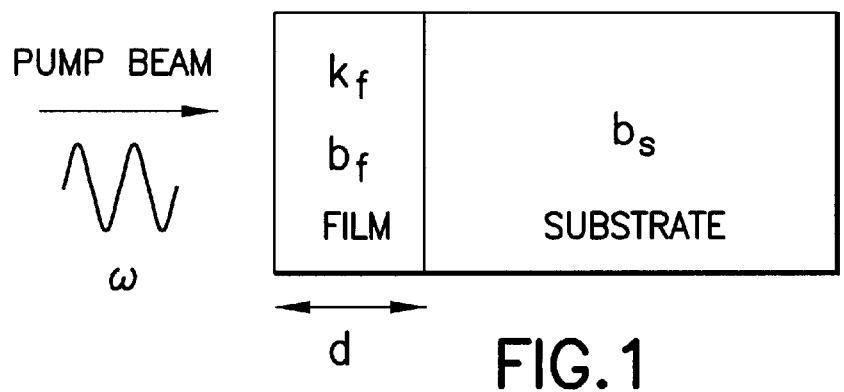
FIG. 1 is a schematic of a two-layer film/substrate specimen, indicating heat diffusion parameters.

Local thermal effusivity of the specimen could be calculated from the two-layer model shown in FIG. 1. Assuming the substrate is semi-infinite normal to the surface and that the heat diffuses one-dimensionally, perpendicular to the surface. The heat source, F (t), is defined as below.

$$F(t) = \sin \omega t \quad \text{(Eq. 1)}$$

Then, the Laplace transform of the surface temperature response, T ($\xi$), is expressed as follows, $$\tilde{T}(\xi) = \frac{1}{b_s\sqrt{\xi}} \frac{\varpi}{\varpi^2 + \xi^2} \frac{\coth(\sqrt{\xi t_f}) + \beta}{\coth(\sqrt{\xi t_f}) + \beta^{-1}} \quad \text{(Eq. 2)}$$

Where $b_s$ is the thermal effusivity of the specimen, $\tau_f$ is the heat diffusion time across the film layer, defined as $\tau_f = d^2/k_f$, and $\beta$ is the thermal diffusivity ratio of the substrate to the film layer.

Performing the inverse Laplace transform to Equation 2, the temperature response, T (t), of specimen's surface is calculated as follows, $$T(t) = A \sin(\omega t - \delta) \quad \text{(Eq. 3)}$$

$$\delta = \frac{3}{4}\pi + \arctan\left[\frac{\cosh^2\sqrt{\frac{\omega t_f}{2}}\left(\tanh\sqrt{\frac{\omega t_f}{2}} + \beta\right)}{\cos^2\sqrt{\frac{\omega t_f}{2}}(\beta - \beta^{-1})\tan\sqrt{\frac{\omega t_f}{2}}}\right] \quad \text{(Eq. 4)}$$

Where $\delta$ is the phase lag of the temperature response to the modulated heating. When the heat diffusion time across the film layer, $\tau_f = d^2/k_f$, is small compared with the inverse of oscillating angular frequency $\omega$ and also to relative thermal effusivity, $\beta$, of specimen to the film, Equation 3 becomes as follows with an approximation.

$$\delta = \frac{3}{4}\pi + \arctan\left[-\frac{1 + \sqrt{\frac{\omega t_s}{2}}}{\sqrt{\frac{\omega t_s}{2}}}\right] \quad \tau_s = \frac{b_f^2 d^2}{b_s^2 \kappa_f} \quad \text{(Eq. 5)}$$

Here, $\tau_s$ is the characteristic time of the heat diffusion in the substrate. According to Equation 5, the phase lag, $\delta$, changes from 45° to 90° when $\omega$ changes from 0 to $\infty$.

Calculation of the ratio of the surface temperature change to the intensity change of heating laser beam is described next.

When $\beta$ and $\tau f$ is small enough, the Equation 2, can be approximated as follows, $$\tilde{T}(\xi) = \frac{1}{b_s\sqrt{\xi}} \frac{\varpi}{\varpi^2 + \xi^2} \frac{1}{1 + \sqrt{\xi t_s}} \quad \text{(Eq. 6)}$$

$$\tau_s = \frac{b_f^2 d^2}{b_s^2 \kappa_f} \quad \text{Eq. 7}$$

Perform the inverse Laplace transform for Equation 6, then the equation becomes $$T(t) = \frac{1}{b_s\sqrt{\xi}} \frac{\phi \sin\left(\omega t + \frac{3}{4}\pi\right) + (1 + \phi)\cos\left(\omega t - \frac{3}{4}\pi\right)}{\phi^2 + (1 + \phi)^2} \quad \text{(Eq. 8)}$$

$$\phi = \sqrt{\frac{\omega \tau_s}{2}} \quad \text{(Eq. 9)}$$

The temperature response at the specimen surface, T (t), is usually written as follows, $$T(t) = A \sin(\omega t - \delta) \quad \text{(Eq. 10)}$$

Then, corresponding amplitude, A, for Equation 6 also can be calculated as shown below.

$$A = \frac{(\beta - \beta^{-1})\tan\psi\sqrt{1 + \frac{(\cosh^2\psi(\tanh\psi + \beta)}{(\cos^2\psi(\beta - \beta^{-1})\tan\psi}}}{b_s\sqrt{\omega}\cosh^2\psi} \quad \text{(Eq. 11)}$$

$$\psi = \sqrt{\frac{\omega \tau_f}{2}} \quad \text{(e.q. 12)}$$

Figure 2:
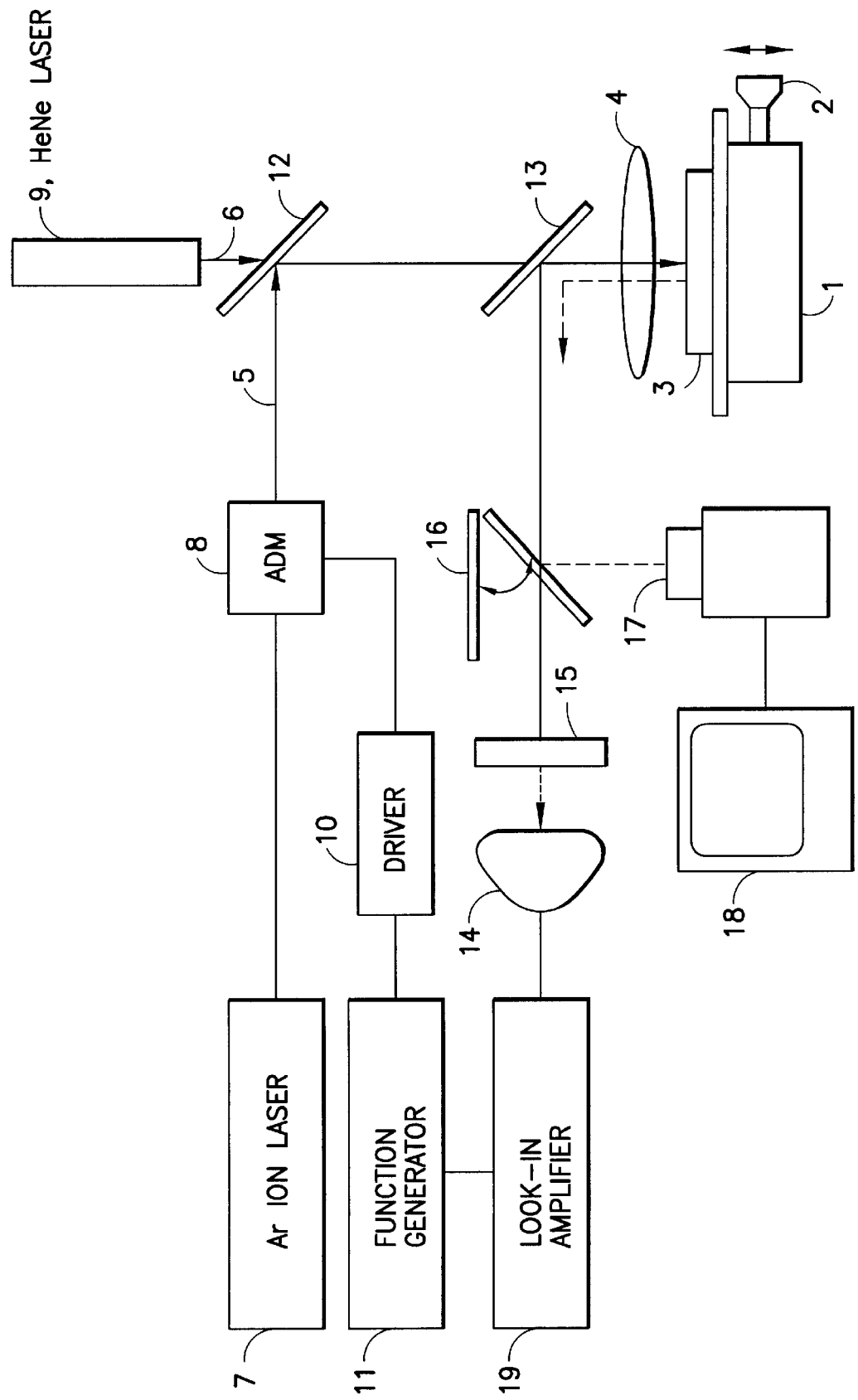
FIG. 2 is a schematic of a thermal effusivity distribution measurement system.

The structure of a thermophysical property microscope according to one embodiment of the present invention will now be described with reference to FIG. 2.

X-Y Stage 1 is able to translate two-dimensionally, and it also has Micrometer 2 for vertical translation with precise adjustment. Specimen 3 is placed on X-Y Stage 1, and the vertical positioning of the stage is adjusted so that laser beams are focused at the surface of the specimen. Heating Laser Beam 5 and Probe Laser Beam 6 are combined and impinged on to the surface of Specimen 3 through Microscopic Optics 4.

Heating Laser System 7, such as 514.5 nm CW Ar laser system, produces Heating Laser Beam 5, and Modulator 8 modulates the beam. Probe Laser Beam System 9, such as CW Helium Neon laser system, produces Probe Laser Beam 6. Driver 10 drives Modulator 8 with a fixed frequency generated by Function Generator 11 to modulate Heating Laser Beam 5. Modulator 8 sinusoidally modulates Heating Laser Beam 5 from Heating Laser System 7 with sinusoidal output signal from Driver 10.

The first Half Mirror 12 reflects the heating beam from the Heating laser system 5 so that the beam travels the optical axis of the microscopic optics 4. In addition, the mirror lets the probe beam 6 from the probe laser system 9 go through and travel the same path with the heating beams.

Heating Laser Beam 5, that is reflected at Half Mirror 12, and Probe Laser Beam 6, that passes through Half Mirror 12, pass through Half Mirror 13 and reach the specimen 3. The beams are reflected at the specimen; then Half Mirror 13 reflects both beams toward Photo Detector 14. Photo Detector 14 is a photodiode in the present embodiment.

Bandpass Filter 15 blocks Heating Laser Beam 5, and only allows Probe Laser Beam 6 to go through. Photo Detector 14 only detects Probe Laser Beam 6. Half Mirror 16 is placed between Half Mirror 13 and Bandpass filter 15; it could be translated on and off the beam path so that the beams either miss or be partially reflected toward CCD Camera 17. CCD Camera 17 detects the partially reflected beams and projects the images of the beams on Monitor 18. The spot sizes and the positions of both Heating Laser Beam 5 and Probe Laser Beam 6 at the surface of the specimen are adjusted precisely.

Probe Laser Beam 6 is detected by Photo Detector 14 and amplified with Lock-In Amplifier 19 to determine its phase lag, δ, respect to reference signal.

Local thermal effusivity is calculated by substituting the known thermal property of the metal thin film and the measured value of phase lag, δ, into Equation 7. Such calculation can be accomplished, for example, by a specialized computer or programmed general purpose computer.

Figure 3:
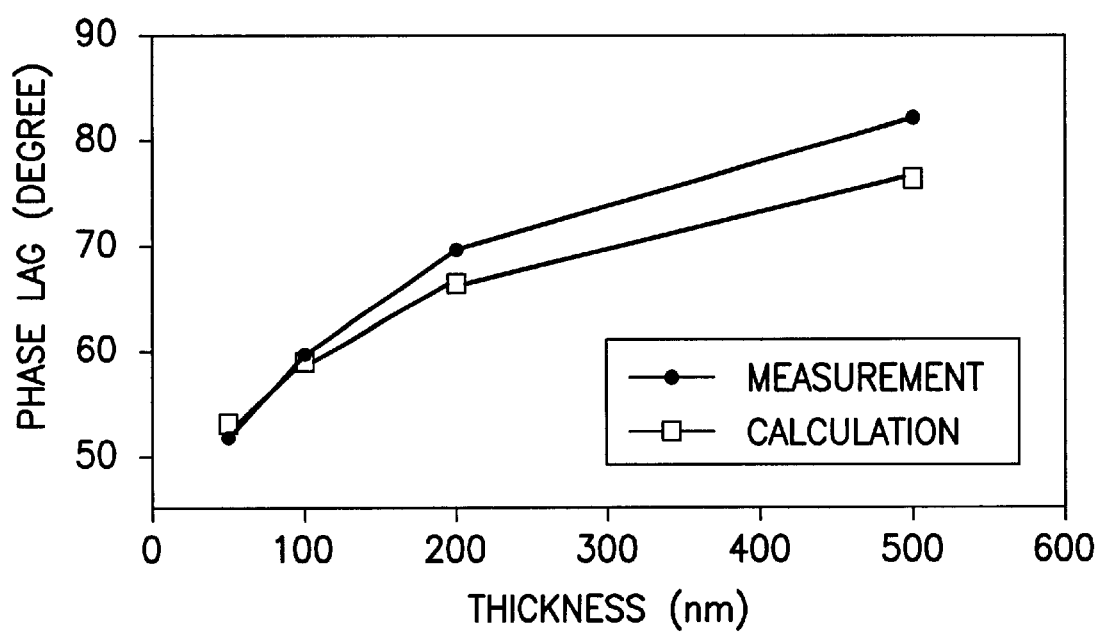
FIG. 3 is a phase lag versus thickness graph illustrating both measured and calculated values.

By way of example, temperature responses of Molybdenum with different thickness are shown in FIG. 3. The values for bulk materials are used for calculation based on Equation 6.

Both measured phase lags and calculated values of phase lag increase with similar dependence on thickness of Molybdenum thin film. Since the thermal effusivity ratio, β of Molybdenum thin film to glass substrate is small, difference between the exact Equation 4 and the approximated Equation 5 is negligibly small. Table 1 shows thermal effusivity values of glass calculated from measured phase legs for the specimens of different film thickness.

TABLE 1

| Thickness(nm) | Phase lag (°) | bs(Js$^{0.5}$/m$^2$K) |
|---|---|---|
| Bulk | — | 1338* |
| 50 | 51.6 | 1700 |
| 100 | 59.8 | 1250 |
| 200 | 69.7 | 1050 |
| 500 | 82.0 | 730 |

INDUSTRIAL APPLICABILITY

This invention could be used directly to measure the thermophysical property distribution of microelectronics devices, such as, large storage media, DVD optical disks, magneto-optical disks, thermoelectrical devices, LSI such as CPUs and RAM, laser diodes, LEDs and power transistors. This invention could also be used to measure the thermophysical property distribution of composite materials that have a superior characteristic over any single material such as Carbon/Carbon composite that is used as the heat-resisting material for nuclear systems and space crafts. This invention will sophisticate heat transport simulation and improve the quality of thermal engineering materials drastically.

It is to be understood that, using high-speed sinusoidal modulation of heating laser beam to measure the distribution of local thermophysical property shortens the measuring time for thermoreflectance technique.

This technique can be applied not only to metals but also to semiconductors, ceramics, and carbon materials by uniformly coating the specimen with a metal thin film.

Then, local thermal effusivity of the substrate, which is under the coated metal thin film, can be calculated from the temperature response of the film surface by the analytical formulation based on the film/substrate two-layer system.

In summary, the present embodiment measures the distribution of the thermophysical properties of micro-scale region on the thin film's surface with high spatial resolution. The surface of Specimen 3 is uniformly coated with metal thin film. In order to heat its surface, Heating Laser Beam 5, which is modulated with Modulator 8, and Probe Laser beam 6, which is impinged on the surface of the specimen, are focused at the same point on the surface through Microscopic Optics 4. The reflection of the probe beam is detected. The surface temperature of the specimen is detected from the reflection of the probe laser beam; the phase lag and relative intensity are measured; and the micro-scale thermophysical property of the specimens are computed. Two-dimensional distribution of local thermophysical property value is obtained by translating the specimen in two-dimensions.

What is claimed is:

1. An apparatus for measuring a thermal effusivity of a specimen having a metallic surface, comprising:

a heating laser producing a heating laser beam which has an intensity and a phase and which locally heats the surface of the specimen producing a heated surface: a modulator for modulating the intensity of the heating laser beam; a probe laser producing a probe laser beam having a first phase which is impinged on the heated surface, said probe laser beam being reflected by the heated surface resulting in a reflected probe laser beam having a second phase, a detector capable of detecting the second phase; and a computer comprising a memory device and a processor disposed in communication with the memory device, the processor configured to calculate the thermal effusivity of the specimen based on a phase lag of the reflected probe laser beam with respect to the phase of the heating laser beam, said specimen having a first and a second layer, wherein said first layer is a thin film and said second layer is a substrate, and wherein the calculation of the thermal effusivity of the specimen is based on the phase lag, δ, wherein $$\delta = \frac{3}{4}\pi + \arctan\left[-\frac{1+\sqrt{\frac{\omega\tau_s}{2}}}{\sqrt{\frac{\tau_s}{2}}}\right], \tau_s = \frac{b_f^2 d^2}{b_s^2 \kappa_f},$$

ω=angular frequency,
$b_f$=thermal effusivity of thin film,
$b_s$=thermal effusivity of substrate,
d=thickness of thin film,
$k_f$=thermal diffusivity of thin film, and
$\tau_s$=Heat diffusion time across the substrate.

2. The apparatus according to claim 1, wherein said processor is further configured to calculate a temperature response from variables comprising the phase lag, an angular frequency of the heating laser beam, a thermal effusivity of the thin film, a thermal effusivity of the thin film, a thermal effusivity of the substrate, a thickness of thin film, a thermal diffusivity of the thin film, and a heat diffusion time across the substrate.

* * * * *